United States Patent [19]
Langlois

[11] Patent Number: 5,853,712
[45] Date of Patent: Dec. 29, 1998

[54] COSMETIC COMPOSITIONS CONTAINING WATER DISPERSIBLE PIGMENT WHICH IS SURFACE TREATED WITH A POLYMER AND PROCESS

[75] Inventor: Anne Langlois, Staines Middlesex, Great Britain

[73] Assignee: The Procter & Gamble Company, Cincinnati, Ohio

[21] Appl. No.: 776,427

[22] PCT Filed: Jul. 13, 1995

[86] PCT No.: PCT/US95/08755

§ 371 Date: Sep. 2, 1997

§ 102(e) Date: Jun. 2, 1997

[87] PCT Pub. No.: WO96/03964

PCT Pub. Date: Feb. 15, 1996

[30] Foreign Application Priority Data

Jul. 30, 1994 [GB] United Kingdom .................. 9415421

[51] Int. Cl.⁶ ..................................... A61K 7/021
[52] U.S. Cl. .......................... 424/78.03; 424/59; 424/63; 424/401
[58] Field of Search ................. 424/401, 70.11, 424/70.17, 63, 78.03, 59

[56] References Cited

U.S. PATENT DOCUMENTS

| | | | |
|---|---|---|---|
| 3,546,008 | 12/1970 | Shields et al. ................ | 117/138.8 |
| 3,734,874 | 5/1973 | Kibler et al. ................ | 260/29.2 |
| 3,779,993 | 12/1973 | Kibler et al. ................ | 260/75 |
| 3,964,500 | 6/1976 | Drakoff ................ | 132/7 |
| 4,233,196 | 11/1980 | Sublett ................ | 260/29 |
| 5,066,485 | 11/1991 | Brieva et al. ................ | 424/63 |
| 5,108,736 | 4/1992 | Schlossman ................ | 424/401 |
| 5,143,671 | 9/1992 | Peters et al. ................ | 264/117 |
| 5,188,831 | 2/1993 | Nicoll et al. ................ | 424/401 |
| 5,534,247 | 7/1996 | Franjac et al. ................ | 424/401 |

OTHER PUBLICATIONS

Todd, et al., "Volatile Silicone Fluids For Cosmetic Formulations", *Cosmetics and Toiletries,* vol. 91, 1976.

Silicon Compounds, Petrarch Systems, Inc., 1984.

deNavarre, *The Chemistry and Manufacture of Cosmetics, Second Edition, vol. IV,* "Fluid Foundation and Blush Make–up" pp. 752–755, 1975.

Porter, Two–in–One Raw Materials, *Cosmetics & Toiletries,* vol. 106, Feb., 1993, pp. 87–92.

*Primary Examiner*—Jyothsna Venkat
*Attorney, Agent, or Firm*—George W. Allen; David L. Suter

[57] ABSTRACT

Colour cosmetic water-in-oil or oil-in-water emulsion compositions wherein the aqueous phase contains a water-dispersible pigment and the oil phase contains an oil-dispersible pigment. The compositions provide improved coverage and wear, with excellent moisturisation, spreadability, product stability and skin-feel, reduced shine and tackiness.

8 Claims, No Drawings

COSMETIC COMPOSITIONS CONTAINING WATER DISPERSIBLE PIGMENT WHICH IS SURFACE TREATED WITH A POLYMER AND PROCESS

FIELD OF THE INVENTION

The present invention relates to cosmetic make-up compositions and more particularly, to pigmented foundation make-up compositions having improved coverage together with excellent moisturisation effectiveness, application characteristics, skin feel and appearance. The present invention also relates to processes for manufacturing cosmetic make-up compositions which provide a convenient means for shade adjustment of the said compositions.

BACKGROUND OF THE INVENTION

A foundation composition can be applied to the face and other parts of the body to even skin tone and texture and to hide pores, imperfections, fine lines and the like. Particularly suitable foundation compositions are available in the form of liquid or cream suspensions, emulsions, and gels.

Such compositions are typically made by incorporating a mixture of pigments into a liquid base. The pigments, commonly based on iron oxides, titanium dioxide, or mixtures thereof, are chosen such that they provide desirable skin tones when the product is applied to the skin. The process for incorporating the pigments often requires a milling stage in order to control the pigment dispersion and thus provide smooth and even coverage of the skin.

As a consequence of variances in raw materials and processsing, batches of finished product may deviate in colour from the target shade. Routine manufacture usually allows for a final shade adjustment of each liquid foundation batch. Since the pigments used cannot usually straightforwardly be added to the finished product without first pre-wetting them in either the oil or water phase, a common practice is to prepare monochromatic batches of finished product specifically for the purpose of final shade adjustment. The need to prepare these monochromatic batches increases the complexity and cost of the manufacturing process.

Quite apart from manufacturing considerations, users of foundation compositions often express dissatisfaction with the degree of coverage of the skin provided by foundations based on conventional pigment systems. Moreover, it is often found that in attempting to improve the amount of coverage by increasing the total pigment level, the naturalness of appearance is adversely affected. It would therefore be desirable to provide a foundation composition containing novel pigment systems which deliver improved coverage and wear without compromising on other properties of the foundation such as skin feel, application characteristics and a natural appearance.

It is accordingly an object of this invention to provide a foundation composition in the form of either a water-in-oil or an oil-in-water emulsion, which exhibits improvements in coverage, together with excellent wear characteristics and a natural appearance.

It is also an object of this invention to provide a foundation composition which provides improvements in coverage and wear without trade-offs in other areas of foundation performance, especially skin feel and application characteristics.

It is a further object of the invention to provide an improved method of manufacturing and shade-matching of colour cosmetic emulsion-form compositions, and, in particular, a method in which the shade can be adjusted to the desired target without the need to use separately prepared monochromatic batches of the compositions.

SUMMARY OF THE INVENTION

According to a first aspect of the invention there is provided a process for manufacturing a colour cosmetic water-in-oil or oil-in-water emulsion composition in which the colour derives from the addition of inorganic or organic pigment, wherein at least a portion of the pigment is made water-dispersible by surface treatment with hydrophilic polymer, and wherein the process comprises adding all or part of the water-dispersible polymer-treated pigment into a pre-formed water-in-oil or oil-in-water emulsion.

According to a further aspect of the invention there is provided a colour cosmetic water-in-oil or oil-in-water emulsion composition wherein the aqueous phase contains a water-dispersible pigment and the oil phase contains an oil-dispersible pigment.

All levels and ratios are by weight of total composition, unless otherwise indicated.

DETAILED DESCRIPTION OF THE DRAWINGS

The compositions of the invention take the form of either water-in-oil or oil-in-water emulsions which contain as essential ingredient a water-dispersible pigment or mixture of pigments. According to one embodiment herein the pigment is a water-dispersible polymer-treated inorganic or organic pigment, more preferably the pigment is a water-dispersible polyester or polyesteramide-treated pigment, especially a water-dispersible polyester-treated pigment. Suitable water-dispersible polyester-treated pigments are those available under the tradename Eastman AQ Treated Pigment (from Eastman Chemical Corporation). The water-dispersible pigment or mixture of pigments is present in an amount of from about 0.1% to about 25%, preferably from about 0.5% to about 15%, and more preferably from about 1% to about 12% by weight.

A preferred water-dispersible polyester or polyester amide for use herein comprises the following repeat units:

(a) at least one difunctional dicarboxylic acid,
(b) at least one difunctional sulfomonomer containing at least one sulfonate group of the formula:

wherein M is H, a metal ion, or a nitrogen-containing basic group, and wherein said sulfonate group is attached directly to an aromatic nucleus and the functional groups of said sulfomonomer are hydroxy, carboxy, amino or a mixture thereof, and (c) at least one glycol or a mixture of a glycol and a diamine having two —NRH groups, the glycol containing two —CH$_2$—OH groups, wherein R is H or an alkyl group of 1 to 4 carbon atoms.

Preferably the difunctional sulfomonomer is present at a level of from about 2 to about 25 mole %, based on a total of all acid, hydroxyl and amino equivalents being equal to 200 mole %.

The water-dispersible polyester-treated pigment used herein comprises from about 1% to about 40%, preferably from about 5% to about 30% by weight thereof of polymer. The average particle size of the treated granulated pigment product is typically between 75 μm and about 1000 μm, with a more typical average particle size being between about 125 μm and about 500 μm, especially between about 150 μm to about 300 μm.

The pigment materials useful in the present invention include water-insoluble, or sparingly water-soluble inorganic and organic pigments, and pearlants commonly used in cosmetics, paints, coatings, and inks, preferably inorganic pigments. Pigment materials suitable herein have a refractive index greater than 1.5, preferably greater than 1.8, more preferably greater than 2. The mean primary particle size of said pigments is preferably greater than 150 nm, more preferably greater than 200 nm.

Typical inorganic pigments include iron oxides of various colors (yellow, red, brown and black), ferric ammonium ferrocyanide (blue), manganese violet, ultramarine blue, chrome oxide (green), titanium dioxide (white) and mixtures of said inorganic pigments. Typical pearlants include mica, bismuth oxychloride and treated mica such as titanated micas.

Exemplary pigments useful in the present invention include the C. I. pigment materials, especially polymer-treated inorganic pigments containing iron oxide or titanium dioxide such as, for example, C. I. Pigment Yellow 42, C. I. Pigment Red 101, C. I. Pigment Black 11 and C. I. Pigment White 6. It is noted that pigments having large amounts of ionizable cations are not preferred since they interfere with the water dispersibility of the polymer.

The polyesters useful herein for treating pigment or mixture of pigments comprise linear, water-dissipatable polymers having an inherent viscosity of at least 0.1 and preferably at least 0.2 and more preferably at least 0.3 (measured as described hereinbelow) and a glass transition temperature ranging from 25° to 90° C. when the polymers are in the dry state. When the polymers contain 1–25 % water of its own weight, the glass transition temperatures ("Tg"s, as measured by differential scanning calorimetry (DSC)) may drop to a lower range usually below 50° C. The polymer compositions useful in this invention are polyesters and polyesteramides described in U.S. Pat. No. 3,546,008, U.S. Pat. No. 3,734,874, U.S. Pat. No. 3,779,993 and U.S. Pat. No. 4,233,196. The polyester or polyesteramide used herein preferably comprise a dicarboxylic acid component, a difunctional sulfomonomer component and a glycol component.

The dicarboxylic acid component of the polyester or polyesteramide comprises aliphatic dicarboxylic acids, alicyclic dicarboxylic acids, aromatic dicarboxylic acids, or mixtures of two or more of these acids. Examples of such dicarboxylic acids include succinic, glutaric, adipic, azelaic, sebacic, itaconic, 1,4-cyclohexanedicarboxylic, phthalic, terephthalic and isophthalic. If terephthalic acid is used as the carboxylic acid component of the polyester, superior results are achieved when at least 5 mole percent of one of the other acids is also used. The preferred dicarboxylic acid component for use herein is isophthalic acid.

It should be understood that use of the corresponding acid anhydrides, esters, and acid chlorides and other substituted derivatives of these acids is included in the term "dicarboxylic acid".

Other suitable acids are disclosed in, for example, U.S. Pat. No. 3,779,993. The difunctional sulfo-monomer component of the polyester or polyesteramide may advantageously be a dicarboxylic acid or an ester thereof containing a metal sulfonate group or a glycol containing a metal sulfonate group or a hydroxy acid containing a metal sulfonate group. The metal ion of the sulfonate salt may be Na+, Li+, K+ and the like. The resulting polyesters or polyesteramides are less readily dissipated by cold water and more readily dissipated by hot water. It is possible to prepare the polyester or polyesteramide using, for example, as sodium sulfonate salt and later by ion-exchange replace this ion with a different ion, and thus alter the characteristics of the polymer. The difunctional monomer component may also be referred to as a difunctional sulfo-monomer and is further described hereinbelow.

Advantageous difunctional sulfo-monomer components are those wherein the sulfonate salt group is attached to an aromatic acid nucleus such as benzene, naphthalene, diphenyl, oxydiphenyl, sulfonyldiphenyl or methylenediphenyl nucleus. Preferred results are obtained through the use of sulfophthalic acid, sulfoterephthalic acid, sulfoisophthalic acid,4-sulfonaphthalene-2,7-dicarboxylic acid, and their esters; metallosulfoaryl sulfonate as described in U.S. Pat. No. 3,779,993. Most preferred for use herein is sulfoisophthalic acid.

When the sulfonate-containing difunctional monomer is an acid or its ester, the polyester or polyesteramide should contain at least 8 mole percent of said monomer based on total acid content, with more than 10 mole percent giving particularly advantageous results. Total acid content is calculated as the sum of (1) moles of component (a) namely dicarboxylic acids, (2) one-half of the moles of carboxyl-containing compounds of component (d), (3) moles of component (c) which are dicarboxylic acids, and (4) one-half of the moles of component (c) which are monocarboxy-containing compounds.

Preferably at least part of the glycol component contains repeating units of a poly(ethylene glycol) of the formula H—(OCH—$_2$—CH$_2$)$_n$—OH wherein n is an integer of 1 to 500, more preferably 2 to about 500. The values of n and the mole percent of poly(ethylene glycol) within the stated range is inversely proportional to the quantity of n within the stated ranges. Thus, when the mole percent is high, the value of n is low. On the other hand, if the mole percent is low, the value of n is high. It is apparent, therefore, that the weight percent (product of mole percent and molecular weight) of the polyethylene glycol is an important consideration because the water dissipatability of the copolyester decreases as the weight percent poly-(ethylene glycol) in the copolyester decreases. For example, if the weight percent of poly(ethylene glycol) is too low, the water dissipatability of the copolyester may be inadequate. Furthermore, the weight percent of poly(ethylene glycol) is preferably adjusted such that it is inversely proportional to the mole percent of the difunctional sulfomonomer because the water dissipatability of the copolyester is a function of both the mole percent sulfomonomer and the weight percent polyethylene glycol.

Examples of suitable poly(ethylene glycols) include relatively high molecular weight polyethylene glycols, some of which are available commercially under the designation "Carbowax", a product of Union Carbide. Diethylene glycol is also especially suitable.

Other useful glycols for preparing copolyesters may consist of aliphatic, alicyclic, and aralkyl glycols. Examples of these glycols include ethylene glycol; propylene glycol; 1,3-propanediol, 2,4-dimethyl-2-ethylhexane-1,3-diol;2,2-dimethyl-1,3-propanediol; 2-ethyl-2-butyl -1,3-propanediol; 2-ethyl-2-isobutyl-1,3-propanediol; 1 ,3-butanediol; 1,4-butanediol; 1,5-pentanediol; 1,6hexanediol; 2,2,4-trimethyl-1,6hexanediol; thiodiethanol; 1,2-cyclohexanedimethanol; 1,3-cyclohexanedimethanol; 1,4-cyclohexanedimethanol; 2,2,4,4-tetramethyl-1,3-cyclobutanediol; p-xylylenediol.

A preferred polyester herein is a diglycol cyclohexanedimethanol isophthalates sulfoisophthalates copolymer. Particularly superior results are achieved when the difunctional sulfo-monomer component is S-sodiosulfoisophthalic acid or its esters and the glycol is a mixture of ethylene glycol or 1,4-cyclohexanedimethanol with diethylene glycol.

Other suitable water-dispersible pigments for incorporation in the compositions of the invention include hydrophilic pigments based on, for example, titanium dioxide and iron oxides.

In a preferred aspect of the invention the compositions herein also contain an oil-dispersible pigment or mixture of pigments in a level preferably from about 0.1% to about 25%, more preferably from about 0.5% to about 15% and especially from about 1% to about 12%. by weight.

Suitable oil-dispersible pigments for use herein can be inorganic and/or organic. Examples of suitable pigments include iron oxides of various colors (yellow, red, brown and black), ferric ammonium ferrocyanide (blue), manganese violet, ultramarine blue, chrome oxide (green), titanium dioxide (white) and mixtures of said inorganic pigments. A mixture of pigments will normally be used.

Also suitable for use herein are coated pigments. The pigments can be treated with compounds such as perfluoroethers, amino acids, silicones, lecithin and ester oils, more preferably with silicones (polysiloxanes) such as polymethyl hydrogen siloxane as described in EP-A-0271925.

The compositions herein take the form of water-in-oil or oil-in-water emulsions in which the oil phase can include one or more silicone oil components. In preferred embodiments thereof the silicone oil comprises volatile silicones or a mixture of volatile silicones and non-volatile silicones. The silicone oil can be included in an amount of from about 1% to about 50% by weight. Suitable volatile silicone oils include cyclic and linear volatile polyorganosiloxanes (as used herein, "volatile" refers to those materials which have a measurable vapour pressure at ambient conditions).

A description of various volatile silicones is found in Todd, et al.. "Volatile Silicone Fluids for Cosmetics", 91 Cosmetics and Toiletries 27–32 (1976).

Preferred cyclic silicones include polydimethylsiloxanes containing from about 3 to about 9 silicon atoms, preferably containing from about 4 to about 5 silicon atoms. Preferred linear silicone oils include the polydimethylsiloxanes containing from about 3 to about 9 silicon atoms. The linear volatile silicones generally have viscosities of less than about 5 mm$^2$·s$^{-1}$ at 25° C., while the cyclic materials have viscosities of less than about 10 mm$^2$.s$^{-1}$. Examples of silicone oils useful in the present invention include: Dow Coming 344, Dow Coming 21330, Dow Coming 345, and Dow Coming 200 (manufactured by the Dow Coming Corporation): Silicone 7207 and Silicone 7158 (manufactured by the Union Carbide Corporation). SF:202 (manufactured by General Electric) and SWS-03314 (manufactured by Stauffer Chemical).

Suitable non-volatile silicones preferably have an average viscosity of from about 1,000 to about 2,000,000 mm$^2$·s$^{-1}$ at 25° C., more preferably from about 10,000 to about 1,800,000 mm$^2$.s$^{-1}$, even more preferably from about 100,000 to about 1,500,000 mm$^2$.s$^{-1}$. Lower viscosity non-volatile silicone conditioning agents, however, can also be used. Viscosity can be measured by means of a glass capillary viscometer as set forth in Dow Coming Corporate Test Method CTM0004, Jul. 20, 1970. Suitable non-volatile silicone fluids for use herein include polyalkyl siloxanes, polyaryl siloxanes, polyalkylaryl siloxanes, polysiloxanes with amino functional substitutions, polyether siloxane copolymers, and mixtures thereof. The siloxanes useful in the present invention may be endcapped with any number of moieties, including, for example, methyl, hydroxyl, ethylene oxide, propylene oxide, amino and carboxyl. However, other silicone fluids having skin conditioning properties may be used. The non-volatile polyalkyl siloxane fluids that may be used include, for example, polydimethylsiloxanes. These siloxanes are available, for example, from the General Electric Company as a Viscasil (RTM) series and from Dow Corning as the Dow Coming 200 series. Preferably, the viscosity ranges from about 10 mm$^2$.s$^1$ to about 100,000 mm$^2$·s.$^{-1}$ at 25° C. The polyalkylaryl siloxane fluids that may be used, also include, for example, polymethylphenylsiloxanes. These siloxanes are available, for example, from the General Electric Company as SF 1075 methyl phenyl fluid or from Dow Coming as 556 Cosmetic Grade Fluid. The polyether siloxane copolymer that may be used includes, for example, a polypropylene oxide modified dimethylpolysiloxane (e.g., Dow Corning DC-1248) although ethylene oxide or mixtures of ethylene oxide and propylene oxide may also be used.

References disclosing suitable silicone fluids include U.S. Pat. No. 2,826,551, Green; U.S. Pat. No. 3,964,500, Drakoff, issued Jun. 22nd, 1976; U.S. Pat. No. 4,364,837, Pader; and GB-A-849,433, Woolston. In addition, *Silicone Compounds* distributed by Petrarch Systems Inc., 1984 provides an extensive (though not exclusive) listing of suitable silicone fluids.

Preferred non-volatile silicones for use herein include polydiorganosiloxanepolyoxy-alkylene copolymers containing at least one polydiorganosiloxane segment and at least one polyoxyalkylene segment, said polydiorganosiloxane segment consisting essentially of

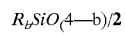

siloxane units wherein b has a value of from about 0 to about 3, inclusive, there being an average value of approximately 2 R radicals per silicon for all siloxane units in the copolymer, and R denotes a radical selected from methyl, ethyl, vinyl, phenyl and a divalent radical bonding said polyoxyalkylene segment to the polydiorganosiloxane segment, at least about 95% of all R radicals being methyl; and said polyoxyalkylene segment having an average molecular weight of at least about 1000 and consisting of from about 0 to about 50 mol percent polyoxypropylene units and from about 50 to about 100 mol percent polyoxyethylene units, at least one terminal portion of said polyoxyalkylene segment being bonded to said polydiorganosiloxane segment, any terminal portion of said polyoxyalkylene segment not bonded to said polydiorganosiloxane segment being satisfied by a terminating radical; the weight ratio of polydiorganosiloxane segments to polyoxyalkylene segments in said copolymer having a value of from about 2 to about 8. Such polymers are described in U.S. Pat. No. 4,268,499. More preferred for use herein are polydiorganosiloxane-polyoxyalkylene copolymers having the general formula:

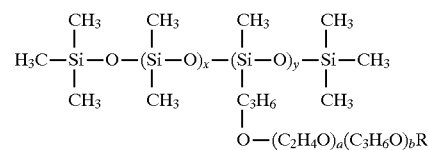

wherein x and y are selected such that the weight ratio of polydiorganosiloxane segments to polyoxalkylene segments is from about 2 to about 8, the mol ratio of a:(a+b) is from about 0.5 to about 1, and R is a chain terminating group, especially selected from hydrogen; hydroxyl; alkyl, such as methyl, ethyl, propyl, butyl, benzyl; aryl, such as phenyl; alkoxy such as methoxy, ethoxy, propoxy, butoxy; benzyloxy; aryloxy, such as phenoxy; alkenyloxy, such as vinyloxy and allyloxy; acyloxy, such as acetoxy, acryloxy and propionoxy and amino, such as dimethylamino.

The number of and average molecular weights of the segments in the copolymer are such that the weight ratio of polydiorganosiloxane segments to polyoxyalkylene segments in the copolymer is preferably from about 2.5 to about 4.0.

Suitable copolymers are available commercially under the tradenames Belsil (RTM) from Wacker-Chemie GmbH, Geschaftsbereich S, Postfach D-8000 Munich 22 and Abil (RTM) from Th. Goldschmidt Ltd,. Tego House, Victoria Road, Ruislip, Middlesex, HA4 OYL. Particularly preferred for use herein are Abil WE 09, Belsil (RTM) 6031, Abil (RTM) B88183 and DC3225C. A preferred silicone herein is known by its CTFA designation as dimethicone copolyol.

The oil phase preferably comprises from about 2% to about 40%, more preferably from about 5% to about 30% by weight of composition of volatile silicones and from about 0.1% to about 10%, preferably from about 0.5% to about 5% of non-volatile silicones, for example polydiorganosiloxane-polyoxyalkylene copolymers.

The compositions herein can also be supplemented by at least one matte finishing agent, inclusive of materials having a refractive index of 1.5 or less. The function of the matte finishing agent is to hide skin defects and reduce shine. Such cosmetically acceptable inorganic agents, i.e., those included in the CTFA Cosmetic Ingredient Dictionary, Third Ed., as spherical silica, hydrated silica, silicone-treated silica beads, mica, talc, polyethylene, bentonite, hectorite, kaolin, chalk, diatomaceous earth, attapulgite and the like may be utilized. Of the inorganic components useful as a matte finishing agent talc, polyethylene, hydrated silica, kaolin, titanium dioxide and mixtures thereof are particularly preferred. Materials suitable for use herein as light-scattering agents can be generally described as spherical shaped inorganic materials having a particle size of up to about 100 microns, preferably from about 5 to about 50 microns, for example spherical silica particles. Highly preferred from the viewpoint of oil absorption and shine reduction, especially in humectant containing products, are spherical silica particles having a specific surface area ($N_2$, BET) of at least 150 $m^2$/g (ASTM-D3663-91) and a pore volume of at least 0.5 ml/g (ASTM-D4222-91).

Another desirable component of the compositions herein is a humectant or mixture of humectants. The humectant or mixture of humectants herein is preferably present in an amount of from about 0.1% to about 30%, more preferably from about 1% to about 25%, and especially from about 3% to about 15% by weight of composition. Suitable humectants are selected from glycerine and polyglycerylmethacrylate lubricant having a viscosity at 25° C. of 300,000 to 1,100,000 mPa.s; a specific gravity at 25° C. of 1 to 1.2 g/ml; a pH of 5.0 to 5.5; a bound water content of 33 to 58%; and, a free water content from 5 to 20%.

The humectant can be incorporated at least partly into the oil phase of the water-in-oil emulsion so as to form a multiphase humectant-in-oil-in-water dispersion. In these embodiments, the oil phase comprises from about 0.1% to about 10%, preferably from about 0.1% to about 3% by weight of humectant on a composition basis. Suitably, the humectant is introduced into the oil phase in the form of a mixture with or incorporated within a particulate lipophilic or hydrophobic carrier material, for example a cross-linked hydrophobic acrylate or methacrylate copolymer as described in detail hereafter.

Suitable polyglycerylmethacrylate lubricants are marketed by Guardian Chemical Corporation under the trademark "Lubrajel". The "Lubrajels" identified as "Lubrajel DV", "Lubrajel MS", and "Lubrajel CG" are preferred in the present invention. The gelling agents sold under these trademarks contain about 1% propylene glycol.

Other suitable humectants include sorbitol, panthenols, propylene glycol, butylene glycol, hexylene glycol, alkoxylated glucose derivatives, such as Glucam (RTM) E-20, hexanetriol, glucose ethers, sodium hyaluronate, and mixtures thereof. Urea is also suitably added as a humectant in the internal aqueous phase.

The panthenol moisturiser can be selected from D-panthenol ([R]-2,4-dihydroxy-N-[3-hydroxypropyl)]-3,3-dimethylbutylbutamide), DL-panthenol, calcium pantothenate, royal jelly, panthetine, pantotheine, panthenyl ethyl ether, pangamic acid, pyridoxin, pantoyl lactose and Vitamin B complex.

In preferred embodiments, the humectant is selected from glycerine and sodium hyaluronate, and mixtures thereof. Chemically, glycerine is 1,2,3-propanetriol and is a product of commerce. When present, sodium hyaluronate is preferably incorporated at a level of from about 0.01% to about 2% by weight. The mixtures are especially valuable herein from the viewpoint of providing enhanced moisturisation.

A further desirable component of the compositions herein is a lubricant. A preferred lubricant herein is a pre-emulsified silicone/polyglyceryl-methacrylate lubricant such as those marketed under the trademark Lubrasil (RTM) from the Guardian Chemical Corporation, 230 Marcus Blvd., Hauppage. N.Y. 11787. In general, Lubrasil (RTA) can be described as a mergence of silicone oil and polyglyceryl-methacrylate lubricant in which the silicone oil is micro-emulsified using high energy to form a complex. Lubrasil also comprises propylene glycol and Polysorbate 20.

Another suitable component of the compositions herein is an aluminium-magnesium-hydroxystearate gelling agent. The aluminium-magnesium-hydroxystearate gelling agent preferably comprises from about 5 to about 40%, more preferably from about 15% to about 25%, especially from about 17% to about 23% by weight thereof of aluminium-magnesium hydroxystearate and from about 95% to about 60%, more preferably from about 85% to about 75%, especially from about 83% to about 77% by weight thereof of a lipophilic oil component which in preferred embodiments is selected from mineral oil, isopropyl myristate, isopropyl palmitate, volatile silicones, castor oil and dioctyl adipate, and mixtures thereof, preferably volatile silicones as described generally above, more preferably cyclomethicone.

The aluminium-magnesium hydroxystearate gelling agent can be included in the compositions of the present invention at a level of from about 0.01% to about 5%, preferably from about 0.05% to about 0.8% especially from about 0.05% to about 0.5%, by weight of composition, wherein the level is defined on an aluminium-magnesium-hydroxystearate active basis, the lower levels being highly preferred from the viewpoint of providing optimum application characteristics.

A preferred aluminium-magnesium-hydroxystearate gelling agent is commercially available from Guinni Chemie GmbH under the tradename Gilugel Sil 5. (CTFA designation: Cyclomethicone pentamer (and) Aluminium-Magnesium-Hydroxy-Stearate). Gilugel Sil 5 is a lipogel comprising about 80% cyclomethicone pentamer and about 20% aluminium-magnesium-hydroxy-stearate. It is particularly valuable in the compositions of the present invention from the viewpoint of improving emulsion stability, spreadability, Theological characteristics and skin feel, and for reducing undesirable tack, shine and greasiness characteristics associated with humectants such as glycerin.

The balance of the composition of the present invention comprises deionized water. The composition preferably comprises from about 15% to about 95%, more preferably from about 20% to about 60% by weight of the oil phase, and from about 5 % to about 85 %, more preferably from about 40% to about 80% by weight of the water phase.

The make-up compositions of the present invention can also comprise a particulate cross-linked hydrophobic acrylate or methacrylate copolymer. This copolymer is particularly valuable for reducing shine and controlling oil while helping to provide effective moisturization benefits. The cross-linked hydrophobic polymer is preferably in the form of a copolymer lattice with at least one active ingredient dispersed uniformly throughout and entrapped within the copolymer lattice. Alternatively, the hydrophobic polymer can take the form of a porous particle having a surface area ($N_2$-BET) in the range from about 50 to 500, preferably 100 to 300m$^2$/g and having the active ingredient absorbed therein.

The cross-linked hydrophobic polymer when used herein is in an amount of from about 0.1% to about 10%, preferably from about 0.3–3% by weight and is preferably incorporated in the external silicone-containing oil phase. The active ingredient can be one or more or a mixture of skin compatible oils, skin compatible humectants, emollients, moisturizing agents and sunscreens. The polymer material is in the form of a powder, the powder being a combined system of particles. The system of powder particles forms a lattice which includes unit particles of less than about one micron in average diameter, agglomerates of fused unit particles of sized in the range of about 20 to 100 microns in average diameter and aggregates of clusters of fused agglomerates of sizes in the range of about 200 to 1,200 microns in average diameter.

The powder material of the present invention which can be employed as the carrier for the active ingredient can be broadly described as a cross-linked "post absorbed" hydrophobic polymer lattice. The powder preferably has entrapped and dispersed therein, an active which may be in the form of a solid, liquid or gas. The lattice is in particulate form and constitutes free flowing discrete solid particles when loaded with the active material. The lattice may contain a predetermined quantity of the active material. The polymer has the structural formula:

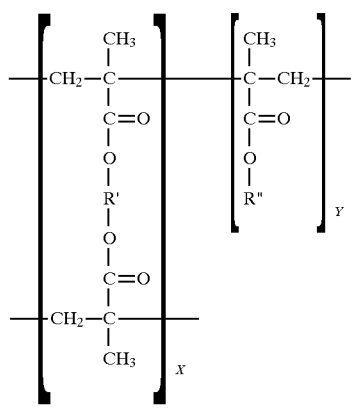

where the ratio of x to y is 80:20, R' is —$CH_2CH_2$— and R" is —$(CH_2)_{11}CH_3$.

The hydrophobic polymer is a highly crosslinked polymer, more particularly a highly cross-linked polymethacrylate copolymer. The material is manufactured by the Dow Corning Corporation, Midland. Mich., USA, and sold under the trademark POLYTRAP (RTM). It is an ultralight free-flowing white powder and the particles are capable of absorbing high levels of lipophilic liquids and some hydrophilic liquids while at the same time maintaining a free-flowing powder character. The powder structure consists of a lattice of unit particles less than one micron that are fused into agglomerates of 20 to 100 microns and the agglomerates are loosely clustered into macro-particles or aggregates of about 200 to about 1200 micron size. The polymer powder is capable of containing as much as four times its weight of fluids, emulsions, dispersions or melted solids.

Adsorption of actives onto the polymer powder can be accomplished using a stainless steel mixing bowl and a spoon, wherein the active is added to the powder and the spoon is used to gently fold the active into the polymer powder. Low viscosity fluids may be adsorbed by addition of the fluids to a sealable vessel containing the polymer and then tumbling the materials until a consistency is achieved. More elaborate blending equipment such as ribbon or twin cone blenders can also be employed. The preferred active ingredient for use herein is glycerine. Preferably, the weight ratio of humectant: carrier is from about 1:4 to about 3:1.

Also suitable as a highly cross-linked polymethacrylate copolymer is Microsponges 5647. This takes the form of generally spherical particles of cross-linked hydrophobic polymer having a pore size of from about 0.01 to about 0.05 $\mu$m and a surface area of 200–300m$^2$/g. Again, it is preferably loaded with humectant in the levels described above.

The compositions of the invention can also contain a hydrophilic gelling agent at a level preferably from about 0.01% to about 10%, more preferably from about 0.02% to about 2%, and especially from about 0.02% to about 0.5%. The gelling agent preferably has a viscosity (1% aqueous solution, 20° C., Brookfield RVT) of at least about 4000 mPa.s, more preferably at least about 10,000 mPa.s and especially at least 50,000 mPa.s.

Suitable hydrophilic gelling agents can generally be described as water-soluble or colloidally water-soluble polymers, and include cellulose ethers (e.g. hydroxyethyl cellulose, methyl cellulose, hydroxypropylmethyl cellulose), polyvinylpyrrolidone, polyvinylalcohol, polyquaternium-10, guar gum, hydroxypropyl guar gum and xanthan gum.

Among suitable hydrophilic gelling agents are acrylic acid/ethyl acrylate copolymers and the carboxyvinyl polymers sold by the B.F. Goodrich Company under the trade mark of Carbopol resins. These resins consist essentially of a colloidally water-soluble polyalkenyl polyether crosslinked polymer of acrylic acid crosslinked with from 0.75% to 2.00% of a crosslinking agent such as for example polyallyl sucrose or polyallyl pentaerythritol. Examples include Carbopol 934, Carbopol 940, Carbopol 950, Carbopol 954, Carbopol 980, Carbopol 951 and Carbopol 981. Carbopol 934 is a water-soluble polymer of acrylic acid crosslinked with about 1 % of a polyallyl ether of sucrose having an average of about 5.8 allyl groups for each sucrose molecule. Also suitable for use herein are hydrophobically-modified cross-linked polymers of acrylic acid having amphipathic properties available under the Trade Name Carbopol 1382, Carbopol 1342 and Pemulen TR-1 (CTFA Designation: Acrylates/10–30 Alkyl Acrylate Crosspolymer). A combination of the polyalkenyl polyether cross-linked acrylic acid polymer and the hydrophobically modified cross-linked acrylic acid polymer is also suitable for use herein. The gelling agents herein are particularly valuable for providing excellent stability characteristics over both normal and elevated temperatures.

Neutraling agents suitable for use in neutralizing acidic group containing hydrophilic gelling agents herein include sodium hydroxide, potassium hydroxide, ammonium hydroxide, monoethanolamine, diethanolamine and triethanolamine.

The make-up compositions herein can additionally comprise an emollient. Emollients suitable for the compositions of the present invention include natural and synthetic oils selected from mineral, vegetable, and animal oils, fats and waxes, fatty acid esters, fatty alcohols, alkylene glycol and polyalkylene glycol ethers and esters, fatty acids and mixtures thereof.

Suitable emollients for use herein include, for example, optionally hydroxy-substituted $C_8$–$C_{50}$ unsaturated fatty acids and esters thereof, $C_1$–$C_{24}$ esters of $C_8$–$C_{30}$ saturated fatty acids such as isopropyl myristate, cetyl palmitate and octyldodecylmyristate (Wickenol 142), beeswax, saturated and unsaturated fatty alcohols such as behenyl alcohol and cetyl alcohol, hydrocarbons such as mineral oils, petrolatum and squalane, fatty sorbitan esters (see U.S. Pat. No. 3,988,255, Seiden, issued Oct. 26 1976), lanolin and lanolin derivatives, such as lanolin alcohol ethoxylated, hydroxylated and acetylated lanolins, cholesterol and derivatives thereof, animal and vegetable triglycerides such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grapeseed oil, and sunflower seed oil and $C_1$–$C_{24}$ esters of dimer and trimer acids such as diisopropyl dimerate, diisostearylmalate, diisostearyldimerate and triisostearyltrimerate.

Preferred emollients are selected from cetearyl isononanoate, isopropyl palmitate, isopropyl isostearate, cetyl octanoate, cetyl acetate, trioctyl citrate, PEG isoceteth-3 acetate, dioctyl maleate, propylene glycol dicaprylate/dicaprate, caprylic/capric triglyceride, mineral oil, PPG-20 methylglucose ether, and lanolin alcohol, and mixtures thereof. These emollients may be used independently or in mixtures and may be present in the composition of the present invention in an amount from about 1% to about 30% by weight, and preferably are present in an amount from about 5% to about 15% by weight of the total composition.

The composition may also contain additional materials such as, for example, fragrances, fillers such as nylon, sun-screens, preservatives, proteins, antioxidants, chelating agents and water-in-oil emulsifiers as appropriate.

Another optional component of the make-up composition is one or more ultraviolet absorbing agents. Ultraviolet absorbing agents, often described as sunscreening agents, can be present in a concentration in the range of between about 1% and about 12% by weight, based on the total weight of composition. Preferably, the UV absorbing agents constitute between about 2% and 8% by weight. More preferably, the UV absorbing agents can be present in the composition in a concentration range of between about 4% and about 6% by weight. Of the ultraviolet absorbing agents suitable for use herein, ultra fine titanium dioxide, ultra fine zinc oxide, benzophenone-3, octyl dimethyl PABA (Padimate O), octyl methoxycinnamate and mixtures thereof are particularly preferred.

A chelating agent can also be incorporated in the make-up composition. A chelating agent is preferably present in the composition in a concentration in the range of between about 0.02% to about 0.10% by weight, based on the total weight of the composition. Preferably, the chelating agent is present in a concentration in the range of between about 0.03% and about 0.07% by weight, based on the total weight of the composition. Among the chelating agents that may be included in the composition is trisodium EDTA.

Another optional but preferred component of the foundation composition is one or more preservatives. The preservative concentration in the foundation composition, based on the total weight of that composition, is in the range of between about 0.2% and about 0.8% by weight, preferably between about 0.4% and about 0.6% by weight. Suitable preservatives for use herein include diazolidinyl urea, methyl paraben and ethyl paraben, and mixtures thereof.

Another optional but preferred component of the foundation composition is a sebum spreading agent. The sebum spreader is present at a level of from about 0.01% to about 5% by weight of composition. A preferred sebum spreading agent is sodium $C_8$–$C_{16}$ isoalkylsuccinyl lactoglobulin sulfonate (Biopol(RTM) OE).

A lower ($C_1$–$C_6$) alcohol may also be present in the foundation of the present invention at a level of from about 0.5% to about 10% by weight of composition. Suitable lower alcohols for use herein include ethanol, hexylene glycol, butylene glycol, propanol and propylene glycol, preferably ethanol.

The make-up compositions of the present invention can be in the form of foundations, blushers, concealers, and the like, preferably as foundations and blushers.

In its process aspect, the present invention broadly relates to a process for manufacturing a colour cosmetic water-in-oil or oil-in-water emulsion composition in which the colour derives from the addition of inorganic or organic pigment, wherein at least a portion of the pigment is made water-dispersible by surface treatment with hydrophilic polymer, and wherein the process comprises adding all or part of the water-dispersible polymer-treated pigment into a pre-formed water-in-oil or oil-in-water emulsion.

The process is particularly valuable for the purposes of shade-matching colour cosmetic emulsion formulae, in which process a proportion of monochromatic water-dispersible polymer-treated pigment is added to the pre-formed water-in-oil or oil-in-water emulsion composition. In the preferred shade matching process, the pre-formed emulsion is pigmented with a polychromatic pigment mixture and the monochromatic, polymer-treated pigment is added incrementally thereto to achieve the desired colour target.

The following Tables are provided to illustrate compositions of the make-up of the present invention:

TABLE 1

| Example | Water-in-oil emulsions | | | | | | | |
|---|---|---|---|---|---|---|---|---|
| | I Wt % | II Wt % | III Wt % | IV Wt % | V Wt % | VI Wt % | VII Wt % | VIII Wt % |
| A. | | | | | | | | |
| Cetyloctanoate | — | — | — | 2.0 | — | — | — | — |
| Cyclomethicone | 5.0 | 20.0 | 12.25 | 15.0 | 8.0 | 5.0 | 8.6 | 15.6 |
| Cyclomethicone/dimethicone copolyol (90:10) | 17.2 | — | 20.0 | 5.0 | 8.0 | 13.0 | 17.2 | 12.5 |
| Propylparaben | 0.25 | 0.25 | 0.25 | 0.25 | 0.25 | 0.25 | 0.25 | 0.25 |

TABLE 1-continued

Water-in-oil emulsions

| Example | I Wt % | II Wt % | III Wt % | IV Wt % | V Wt % | VI Wt % | VII Wt % | VIII Wt % |
|---|---|---|---|---|---|---|---|---|
| Laureth-7 | 0.5 | 0.5 | — | 0.5 | — | 0.5 | — | 0.5 |
| Dioctyl maleate | — | — | — | — | 10.0 | — | — | — |
| Dimethicone | — | — | — | 3.0 | 5.0 | 10.0 | — | — |
| Benzophenone-3 | — | — | — | — | — | 2.0 | — | — |
| Propylene glycol dicaprylate/ dicaprate | — | — | — | 5.0 | — | 10.0 | — | — |
| Octyl methoxycinnamate | 10.0 | — | 1.0 | — | — | — | 5.0 | — |
| B. | | | | | | | | |
| Titanium Dioxide | 8.25 | 6.0 | 1.5 | — | 8.0 | 12.0 | 8.25 | 8.25 |
| Titanium Dioxide treated (Aluminium hydrate, stearic acid) | 0.25 | 0.5 | 3.0 | — | 0.25 | — | 0.25 | 0.25 |
| Titanated Micas | 0.1 | 0.1 | 0.1 | 0.25 | 1.0 | — | 0.1 | 0.1 |
| Talc | 3.39 | 4.5 | 6.0 | 0.7 | 0.7 | — | 3.39 | 4.0 |
| Nylon | — | — | — | — | 0.5 | — | — | — |
| C. | | | | | | | | |
| Cyclomethicone/dimethicone copolyol (90:10) | 1.85 | 1.5 | 1.85 | 5.0 | 1.0 | 1.0 | 1.85 | — |
| Acrylates Copolymer | — | — | — | — | 1.0 | — | — | — |
| Acrylates Copolymer (loaded with glycerine) | — | — | 6.0 | — | — | 1.0 | 1.0 | — |
| D. | | | | | | | | |
| Yellow Iron Oxide | 1.2 | — | 0.6 | 0.4 | 1.2 | 1.2 | 1.2 | 1.2 |
| Red Iron Oxide | 0.49 | — | 0.6 | 0.49 | 0.49 | 0.2 | 0.6 | 0.42 |
| Black Iron Oxide | 0.16 | — | 0.24 | 0.1 | 0.1 | 0.24 | 0.24 | 0.22 |
| Ultramarine Blue | — | — | — | 0.1 | — | — | — | — |
| Cyclomethicone | — | — | — | — | 0.68 | — | — | — |
| Silica (spheron P1500) | 4.0 | — | 1.0 | — | 0.1 | — | — | — |
| Silica beads (Spheron L1500) | — | — | 3.0 | — | — | 0.1 | 0.5 | 0.5 |
| E. | | | | | | | | |
| Synthetic Wax | 0.1 | 0.5 | 0.5 | 0.1 | — | — | — | 0.1 |
| Arachidyl behenate | 0.3 | — | — | 0.3 | — | 0.3 | 0.3 | 0.3 |
| Stearic Acid | — | — | — | — | — | — | 2.5 | — |
| Palmitic Acid | — | — | — | — | — | 2.5 | — | — |
| F. | | | | | | | | |
| Trihydroxy-stearin | 0.3 | 0.3 | 1.5 | 1.5 | — | — | — | 0.3 |
| Cyclomethicone | 1.0 | 4.0 | — | — | 4.0 | 4.0 | 4.0 | 1.0 |
| Beeswax | 1.5 | 1.2 | — | — | 1.3 | — | — | — |
| Abil WEO9 | — | 3.0 | — | — | — | — | — | — |
| Palm Oil | — | — | — | — | 4 | — | — | — |
| Al Mg hydroxy stearate/ cyclomethicone (20:80) | 0.5 | — | 1.8 | 1.5 | 10.0 | 3.0 | 3.0 | — |
| G. | | | | | | | | |
| Ethylene brassylate | 0.05 | 0.05 | 0.05 | 0.05 | 0.05 | 0.05 | 0.05 | 0.05 |
| BHT | 0.05 | 0.05 | 0.05 | 0.05 | 0.05 | 0.05 | 0.05 | 0.05 |
| H. | | | | | | | | |
| Deionized water | <— — | — — | — — | to 100 | — — | — — | — — | — —> |
| Methyl paraben | 0.12 | 0.15 | 0.15 | 0.12 | 0.12 | 0.12 | 0.15 | 0.12 |
| Propylene glycol | 8.0 | 8.0 | — | — | 1.75 | 8.00 | — | — |
| Sodium chloride | 2.0 | 1.4 | 1.4 | 0.5 | 2.0 | 2.0 | 2.5 | 2.0 |
| Sodium dihydroacetate | 0.3 | 0.3 | 0.3 | 0.8 | 0.8 | 0.3 | 0.8 | 0.3 |
| Glycerine | 4.5 | 15.0 | 10.0 | 5.0 | 6.5 | 10.0 | 3.0 | 10.0 |
| Trisodium EDTA | — | — | — | — | — | 0.01 | — | — |
| Phenoxyethanol | — | — | 0.5 | — | — | 0.2 | — | — |
| Titanium dioxide | 1.5 | 6.0 | 6.0 | 6.0 | 3.0 | 3.0 | 3.0 | 0 |
| Polymer pigment 1 | 0.8 | 0.5 | 0.5 | 0.8 | 0.8 | 0.5 | 0.5 | 0.8 |
| Polymer pigment 2 | 0.3 | 0.3 | 0.3 | 0.3 | 0.3 | 0.3 | 0.3 | 0.3 |
| Polymer pigment 3 | 0.2 | 0.2 | 0.2 | 0.4 | 0.2 | 0.2 | 0.2 | 0.2 |
| Triethanolamine | — | — | — | — | — | — | 0.75 | — |
| Allantoin | — | — | 0.1 | — | — | — | — | — |
| Biopol OE | — | 0.5 | — | — | — | 0.5 | — | — |
| Ethanol | — | 6.0 | — | — | — | 2.0 | — | — |
| Panthenol | — | — | 3.0 | — | — | 2.0 | — | — |
| Hydroxyethyl-cellulose | — | — | 0.1 | — | — | — | — | — |
| Ultra fine zinc oxide | — | — | — | 0.2 | 0.2 | — | — | — |
| Sodium hyaluronate | — | 0.05 | 0.08 | 0.1 | — | — | 0.2 | — |

TABLE 1-continued

Water-in-oil emulsions

| Example | I Wt % | II Wt % | III Wt % | IV Wt % | V Wt % | VI Wt % | VII Wt % | VIII Wt % |
|---|---|---|---|---|---|---|---|---|
| I. | | | | | | | | |
| Deionized Water | — | — | — | — | 10.0 | — | — | — |
| Magnesium Aluminum Silicate | — | — | — | — | 0.2 | — | — | — |
| J. | | | | | | | | |
| Propylene Glycol | — | — | — | 2.0 | — | — | — | — |
| Xanthan Gum | — | — | — | 0.08 | — | — | — | — |
| K | | | | | | | | |
| Essential Oils | — | — | — | 0.20 | — | — | — | — |
| Perfume Oil | — | 0.25 | — | 0.20 | — | — | — | — |
| Vitamin A palmitate | 0.05 | 0.05 | — | — | — | — | — | — |
| Vitamin E acetate | — | — | 1.0 | — | 2.0 | — | — | — |
| L. | | | | | | | | |
| Aloe Vera Gel | — | — | 3.0 | — | — | — | — | — |
| Chamomile Extract | — | — | 0.1 | — | — | — | — | — |

Polymer pigments 1, 2 and 3 are water-dispersible polymer treated red, yellow and black iron oxides, wherein the polymer is a diglycol cyclohexanedimethanol isophthalates sulfoisophthalates copolymer.

The various components listed in Table 1 have been segregated into groups, the constituents of each group being mixed together before being added to members of the remaining groups in accordance with the procedures set forth below.

In the first step, the mixture of components of phase A is stirred for approximately 5 minutes with sheer mixing until homogeneous. With high speed shear mixing, the materials of phase B are added gradually to A and the batch is mixed for 35 minutes until dispersed.

The components of phase C and then phase D are slowly added to the mixture of phases A and B with high shear mixing until dispersed. Silica is added at this point and dispersed through the mixture.

The components of phase E are added into the resulting batch which is then heated to 84° C. and mixed until dispersed. The vessel is cooled to 45° C. and the premixed phase F is added. The batch is mixed until homogeneous. The mixture is cooled to 30° C. and phase G is added.

A premix of phase H is made by mixing all the components until completely dispersed. At 30° C. the premix of phase H is added sparingly to the batch mixture with high shear, ensuring that there is no excess water on the surface. The mixture is then mixed for 15 minutes. Finally phases I, J, K, and L are added.

The resulting make-up composition is ready for packing.

TABLE 2

Oil-in-water emulsions

| Example | I Wt % | II Wt % | III Wt % |
|---|---|---|---|
| A. | | | |
| Glyceryl monostearate/ PEG-100 stearate | 0.8 | 2.5 | 1.0 |
| PEG-10 soya sterol | 1.5 | — | 2.0 |
| Sorbitan monostearate | 2.0 | 0.1 | 2.25 |
| Propylene glycol dicaprylate/dicaprate | 2.5 | 10.0 | 5.0 |
| Dioctyl maleate | 7.7 | 3.0 | 15.0 |
| Squalane | — | — | 2.5 |
| Octyl methoxycinnamate | — | — | 5.0 |
| Benzophenone-3 | — | — | 2.0 |
| Hydroxylated lecithin | 0.5 | — | — |
| Lecithin | 2.0 | 3.5 | 0.4 |
| Vitamin E linoleate | — | — | 0.5 |
| Cetyl alcohol | — | — | 1.0 |
| Cetearylisononanoate | 5.25 | — | 5.0 |
| Mineral oil | 1.5 | — | 2.0 |
| Beeswax | 0.5 | — | 0.5 |
| Glyceryl monostearate | 2.25 | — | — |
| Phenoxethol | 0.21 | 0.21 | 0.21 |
| BHA | — | — | 0.1 |
| Parabens | 0.09 | 0.09 | 0.09 |
| Treated iron oxides - yellow | 0.3 | — | 0.3 |
| Treated iron oxides - red | 0.2 | — | 0.2 |
| Treated iron oxides - black | 0.05 | — | 0.05 |
| Treated TiO2 | 3.0 | 2.0 | 10.0 |
| B. | | | |
| Deionized Water | 1.2 | 1.2 | 2.0 |
| Titanium Dioxide | 6.0 | 8.0 | 3.0 |
| Titanated Micas | — | — | 2.4 |
| Talc | 1.0 | — | 3.0 |
| Treated iron oxides - yellow | — | 0.34 | 0.5 |
| Treated iron oxides - red | — | 0.46 | 0.4 |
| Treated iron oxides - black | — | 0.08 | 0.14 |
| Ultramarine blue | — | 0.02 | 0.05 |
| Ammonium acrylate copolymer | 0.2 | 0.2 | 0.2 |
| Nylon | — | — | 0.5 |
| C. | | | |
| Deionized water | <— — to 100% — —> | | |
| Triethanolamine | 0.5 | 0.5 | 0.5 |
| Methyl paraben | 0.1 | 0.1 | 0.1 |
| Trisodium EDTA | 0.01 | 0.01 | 0.05 |
| Allantoin | 0.09 | 0.09 | 0.2 |
| Phenoxethol | 0.42 | 0.42 | 0.42 |
| Parabens | 0.18 | 0.18 | 0.18 |
| Glycerine | 5.0 | — | 10.0 |
| Methyl gluceth-20 | 5.0 | 5.0 | — |

TABLE 2-continued

Oil-in-water emulsions

| Example | I Wt % | II Wt % | III Wt % |
|---|---|---|---|
| D. | | | |
| Potassium cetylphosphate | 1.0 | 1.0 | 0.5 |
| E. | | | |
| Methyl methacrylate cross-polymer | — | 0.5 | 3.0 |
| F. | | | |
| Deionized Water | 2.0 | 2.0 | 2.0 |
| Magnesium Aluminum Silicate | 0.2 | 0.25 | 0.15 |
| G. | | | |
| Deionized Water | 2.0 | 2.0 | 2.0 |
| Propylene glycol | 2.0 | 8.0 | — |
| Xanthan Gum | 0.16 | 0.08 | 0.16 |
| Hydroxyethylcellulose | 0.1 | 0.1 | 0.05 |
| H. | | | |
| Lubrasil | 0.5 | 1.0 | — |
| I. | | | |
| Cyclomethicone/Dimethiconol | 15.0 | 3.0 | — |
| Dimethicone/Dimethiconol | 2.0 | 10.0 | — |
| J. | | | |
| Isododecane | 2.0 | — | — |
| K. | | | |
| Silica beads (Spheron L1500) | 2.5 | 0.5 | — |
| L. | | | |
| Essential Oils | 0.2 | — | — |
| Perfume Oil | 0.2 | — | — |
| Vitamin A palmitate | — | — | 0.05 |
| M. | | | |
| Aloe Vera Gel | — | 3.0 | 3.0 |
| Chamomile Extract | — | — | 0.1 |

These iron oxides are treated with a diglycol cyclohexanedimethanol isophthalates sulfoisophthalates copolymer.

The various components listed in Table 2 have been segregated into groups, the constituents of each group being mixed together before being added to members of the remaining groups in accordance with the procedures set forth below.

In the first step, the mixture of components of phase B is stirred with shear mixing until homogeneous. With slow speed shear mixing at 65°–75° C., the materials of phase C are admixed individually in order as given in the formulations.

The components of phase A are mixed until dispersed. The ingredients of phase K are then added to phase A with high shear mixing.

The magnesium aluminium silicate of phase F is prehydrated for at least 30 minutes at 50° C. and is then added to the aqueous phase C and thoroughly dispersed therein.

The deionised water/propylene glycol (or glycerine)/xanthan gum slurry of phase G is added to heated aqueous phase C at 65°–67° C. and phase B is slowly added to phase C. Stirring is continued until homogeneous, while maintaining a temperature of 65°–67° C. Component D is then added to the resulting mixture with stirring.

The components of F and G are added to the mixture with slow stirring for 5 minutes until homogeneous. Then component E is added to the mixture with slow stirring until completely incorporated.

The resulting oil phase of components A and K is then added to the water phase of components B, C, D, E, F and G and agitated via stirring to emulsify the mixture at a temperature of about 65–67 temperature of 65°–67° C. The resulting mixture is cooled down.

At about 35° C., the Lubrasil of phase H is added to the resulting batch and mixed until homogeneous. At about 35° C., the silicone mixture of phase I is added to the resulting batch. The resulting mixture is agitated with low-speed mixing until a gel-like consistency is obtained, generally within about 1–2 minutes. At 30° C., the perfume oil and essential oils of phase L are added and then the components of phase M are added.

The resulting make-up composition is ready for packing.

The make-up compositions of the Examples exhibit improved coverage and wear, with excellent moisturisation, spreadability, product stability and skin-feel, reduced shine and tackiness and a uniform coverage giving a natural skin appearance.

The process is repeated for each of the examples above, with the exception that 10% of the total amount of each of polymer pigments 1, 2 and 3 is reserved for addition as a final step. Before packing, the colour of the make-up composition is spectroscopically compared to the desired target and the reserved amounts of the polymer pigments are dispersed as necessary into the make-up composition using low-shear mixing until the desired colour target is met.

The shade-matching process of the Examples provides a method in which the shade of the finished product can be adjusted to the desired target in a convenient manner without the need to use separately prepared monochromatic batches of the finished compositions.

I claim:

1. A color cosmetic water-in-oil or oil-in-water emulsion wherein the aqueous phase contains from about 0.1% to about 25% by weight of the emulsion of a water dispersible pigment selected from the group consisting of iron oxide and titanium dioxide pigment and the pigment is surface treated with diglycol cyclohexanedimethanol isophthalates and sulfoisophthalates copolymer and the oil phase contains from about 0.1% to about 25% by weight of the emulsion of an oil-dispersible pigment.

2. A composition according to claim 1 wherein the surface-treated water-dispersible pigment comprises from about 1% to about 40% by weight thereof of the surface-treating polymer.

3. A composition according to claim 1 wherein the emulsion composition comprises from about 0.5% to about 15% by weight of the water-dispersible pigment.

4. A composition according to claim 1 wherein the emulsion composition comprises from about 1 % to about 12% by weight of the water-dispersible pigment.

5. A composition according to claim 1 wherein the emulsion composition comprises from about 0.5% to about 15% by weight of the oil-dispersible pigment.

6. A composition according to claim 1 wherein the emulsion composition comprises from about 1 % to about 12% by weight of the oil-dispersible pigment.

7. A composition according to claim 2 wherein the surface-treated water-dispersible pigment comprises from about 5% to about 30% by weight thereof of the surface-treating polymer.

8. A process for manufacturing a color cosmetic water-in-oil or oil-in-water emulsion composition in which the color derives from the addition of titanium dioxide or iron oxide pigment and wherein at least a portion of the pigment is made water-dispersible by surface treatment with a diglycol cyclohexanedimethanol isophthalates and sulfoisophthalates copolymer, which process comprises adding all or part of the water-dispersible, polymer-treated pigment into a pre-formed water-in-oil or oil-in-water emulsion.

* * * * *